United States Patent [19]

Jacobson et al.

[11] Patent Number: 4,643,901

[45] Date of Patent: Feb. 17, 1987

[54] YEAST STRAINS, METHOD OF PRODUCTION AND USE IN BAKING

[75] Inventors: Gunnard K. Jacobson, Brown Deer; Nayankumar B. Trivedi, Bayside, both of Wis.

[73] Assignee: Universal Foods Corporation, Milwaukee, Wis.

[21] Appl. No.: 503,323

[22] Filed: Jun. 10, 1983

[51] Int. Cl.$^4$ .................. A23L 1/28; C12N 15/00; C12N 1/18; C12R 1/865

[52] U.S. Cl. .................. 426/62; 435/172.2; 435/256; 435/942; 935/97

[58] Field of Search .................. 426/60, 62; 435/942, 435/256, 172.2; 935/97

[56] References Cited

U.S. PATENT DOCUMENTS

| | | | |
|---|---|---|---|
| 3,993,783 | 11/1976 | Langejan et al. | 426/60 |
| 4,328,250 | 5/1982 | Clément et al. | 426/60 |
| 4,341,871 | 7/1982 | Langejan et al. | 426/60 |
| 4,368,263 | 1/1983 | Ball et al. | 935/97 |
| 4,431,737 | 2/1984 | Olivieri et al. | 435/256 |
| 4,450,238 | 5/1984 | Vitobello et al. | 435/256 |

OTHER PUBLICATIONS

Yamamoto, Masahiro – "Fusion of Yeast Protoplasts" (1977) (2340 Agricultural & Biological Chemistry, vol. 41, No. 9).

*Primary Examiner*—Christine M. Nucker
*Attorney, Agent, or Firm*—Neuman, Williams, Anderson & Olson

[57] ABSTRACT

Novel biologically pure quick acting bakers yeast strains NRRL Y-15338 and NRRL Y-15339 are provided which show good performance in sweet, regular, and lean doughs, and superior performance in sweet and lean doughs, particularly when used in the active dry yeast form. A method of obtaining these and other novel bakers yeast strains by hybridization via protoplast fusion of petite mutants is also provided. Improved methods of baking using these novel bakers yeasts especially in the active dry yeast form are also provided.

10 Claims, No Drawings

YEAST STRAINS, METHOD OF PRODUCTION AND USE IN BAKING

BACKGROUND OF THE INVENTION

1. Field of the Invention

This invention relates to improved biologically pure, novel strains of quick acting general purpose bakers yeast which show good performance in sweet, regular and lean dough systems and especially superior performance in sweet and lean doughs, and methods of obtaining the same from existing strains of quick acting bakers yeast by hybridization via protoplast fusion of petite mutants of such quick acting yeast, to quick acting active dry yeast made from these strains yeast and to improved baking methods using said novel yeast strains in active dry yeast form.

2. Description of the Prior Art

So-called quick acting strains of the yeast *Saccharomyces cerevisiae* are known and are commercially available in active dry yeast form. These yeasts are generally characterized by the rapid production of a relatively large amount of carbon dioxide in a given time frame when mixed with doughs which basically contain flour and water, and which usually fall into one of the general categories of sweet, lean, or regular doughs. The value of these so called quick bakers yeasts are especially significant in the commercial baking field particularly when used in the active dry yeast form containing low amounts, i.e. 4 to 8 percent, of moisture. Some of the quick acting yeasts which are available are characterized by a tolerance to sweet doughs which contain substantial amounts of sugar, i.e., up to about 20 to 25% sugar. Generally speaking, these fast acting, or so called quick yeasts of commerce have only moderate activity with a regular or straight dough which contains 4 to 5% sugar and relatively poor activity in lean doughs which contain no added sugar. Likewise quick lean dough yeast of commerce are not useful for sweet doughs. Actually, it is generally acknowledged in the baking industry that improvements in performance of yeast in sweet dough formulations is at the expense of lean dough performance and vice versa.

This recognition has led to commercial yeast producers manufacturing separate yeast products for commercial use in either sweet doughs or lean doughs. Insofar as it is presently known, there is no single yeast strain which demonstrates quick and superior leavening activity in both lean doughs and sweet doughs.

SUMMARY OF THE INVENTION

This invention relates to novel strains of the bakers yeast *Saccharomyces cerevisiae* which are characterized by quick leavening action and particularly by suitability for use in leavening of bakery products made from both lean doughs which contain no sugar and high sugar containing or so called sweet doughs.

This invention also relates to methods of forming novel hybrids of yeast strains via protoplast fusion of petite mutants of certain yeast strains, the use of these novel yeast strains in the production of active dry yeast for use in the bakery industry, and to improved baking methods using these novel yeast strains in the active dry yeast form.

Broadly, the procedure and method of the present invention involves hybridizing, by protoplast fusion of petite mutants of dissimilar, sexually incompatible, heterozygotic strains of the yeast *Saccharomyces cerevisiae*.

More particularly, the process of the present invention involves the steps of (a) growing two dissimilar yeasts on a fermentable sugar-containing culture medium, the said yeast strains being characterized by a relatively high tolerance to sugar and a capacity for proliferative growth on nutrient substrates in which glycerol is the sole carbon source nutrient, (b) isolating spontaneous petite mutant yeast colonies which are characterized by their inability to metabolize glycerol, (c) enzymatically removing the cell wall material to produce yeast protoplasts, (d) hybridizing the yeast by fusing the yeast protoplasts then in the presence of polyethylene glycol, (e) recovering the fused hybridized yeast cells from the fusion step, and (f) growing the protoplast fusion yeast cells on a nutrient substrate with glycerol as the sole carbon nutrient source, and (g) recovering the yeast cells produced by said procedure.

Broadly, the yeast strains used to generate the petite mutants are *Saccharomyces cerevisiae* strains which demonstrate relatively high osmotolerance and relatively quick acting characteristics when placed in dough formulations containing flour, water and sugar. Such yeasts are well known commercially and have also been referred to in the literature—see for example U.S. Pat. No. 3,993,783 which refers to strains Ng 2031 and Ng 2103 and U.S. Pat. No. 3,394,008 which refers to strains Ng 740 and Ng 1777, said accession numbers having been assigned to yeasts deposited in the Central Bureau Voor Schimmelcultures, Delft, Netherlands.

Preferably the strains used in the hybridization and protoplast fusion procedure of this invention are also characterized by the fact that the strains cannot mate in nature nor can the petite mutants arising from the culture of said yeast be mated. The yeasts are also characterized by their capacity to grow on substrates in which glycerol is the sole carbon source nutrient.

The two seletced yeast strains chosen as petite mutant sources, are first cultivated on nutrient substrates in which a fermentable sugar such as glucose, or in some caases sucrose, is the sole carbon nutrient source. Such growth procedure gives rise to spontaneous petite mutant colonies which are distinguished from the grande colonies by size and color. These colonies are treated with the dye 2,3,5-triphenyl tetrazolium chloride (TTC) which stains normal colonies pink while petite colonies remain white.

In a typical procedure, the petite colonies are isolated and sub-cloned on yeast extract, peptone and dextrose media (YPD) plates. The sub-clones are then replicated on yeast extract, peptone, glycerol (YPGLY) plates to confirm and select the desired petite mutants which do not grow on substrates having glycerol as the carbon nutrient source. The selected sub-clone isolates are then separately grown on a YPD liquid broth culture for 48 hours and harvested by separation (centrifugation) from the nutrient media which is washed from the cells. The sub-clone cultures of the petite mutant yeast cells are then treated with enzymes (i.e., zymolyase or β-glucuronidase) to remove the cell walls thereby creating yeast protoplasts which are thoroughly washed.

The separate yeast protoplasts thus produced from the source yeast petite colonies following either of the two protocols, are then combined and suspended in a fusion buffer of polyethylene glycol (mol. wt. 4000–6000), sorbitol and a calcium salt, and incubated for a period of from 15 to 30 minutes, preferably about 30 minutes, and the fusion buffer is then removed.

The recovered cells are incubated overnight in a recovery broth comprising hypertonic glucose which contains 1% yeast extract, 0.8 molar sorbitol and 0.2% glucose.

Following incubation in recovery broth, the cells were plated on hypertonic glycerol agar which consisted of 1% yeast extract, 2% peptone, 3% glycerol, 0.8M sorbitol, and 3% agar,. Only fusion products successfully proliferate on glycerol substrates.

The hybrid yeast cells arising on hypertonic glycerol were streaked to YPD, and selected clones were replicated to sucrose, glycerol and sporulation media (potassium acetate) plates. Selected clones which grew on all media were cultured for about 48 hours in a YPD broth. Clones yielding 0.3 grams of yeast solids/100 mL of broth were selected for further evaluation.

The selected protoplast fusion yeast hybrids are further selected by gas production (carbon dioxide) tests in three test dough systems for lean and sweet dough activity. Fifty (50) mg (dry weight) of yeast were added to the model mixes shown below. The yeast was suspended in the 15 mL of added water.

A.
  Flour 20 g (4X, Pillsbury)
  Water 15 mL
B.
  Flour 20 g
  Water 15 mL
  NaCl 0.4 g
C.
  Flour 20 g
  Water 15 mL
  NaCl 0.4 g
  Sucrose 4 g The dough was mixed for 45 to 60 seconds and the mix incubated at 30° C. for four hours, during which the gas volume was measured at half hour (30 min) intervals. Strains which produce more than 300 mL of carbon dioxide per 100 mg yeast solids for test A and at least 200 mL of gas for tests B and C over a four hour test period are selected.

An active dry yeast is readily prepared from these hybrids by standard procedures, i.e. growing the yeast strains in typical multi-stage batch fermentation stages using a molasses as the nutrient carbon source. The yeast harvested from the last or trade fermenter is concentrated and dried under temperature and humidity conditions that maintain its viability, to final moisture contents of between about 4 and 8%, preferably about 6%.

Two novel strains produced by the procedure of this invention were deposited with the Northern Regional Research Laboratory, Peoria, Ill., accession numbers NRRL Y-15338 and NRRL Y-15339.

The yeast strain *Saccharomyces cerevisiae* NRRL Y-15338 has the following physical description:

Cells grown three days at room temperature in 10° Brix malt extract are ovoid to ovate-deltoid, to ellipsoidal. Cell sizes (lenth×width) of unmatured daughter cells are in the 5.8–7.0×4.7–5.8 micron range. Mature cells range from 9.3–11.7×5.8–8.2 microns. Most cells are in the 9×7 micron range. On 1% potassium acetate, 0.1% glucose, 0.25% yeast extract sporulation medium, sporulation efficiency is 77.9±9.4%. The frequency of asci with four spores was 5.59±1.64%. Four spored asci are rhomboid or tetrahedral. Ascospores are spherical to prolate-ellipsoidal in shape.

The culture ferments α-methylglucoside and melezitose slowly. Gas first appears in α-methylglucoside broth durham tubes after 3 to 5 days with a standardized 200,000 cell/mL inoculum. With melezitose, first gas appeared in 3 days. Trehalose was not fermented in 21 days of observation. Protocols used were those of Lodder, North Holland Publishing Co., Amsterdam (1970), pp. 66–73.

The colony morphology on uncrowded (15–30 colonies/plate) Wallerstein's Laboratory (WL) medium after 5 days is dark green in color, peaked-pulvinate in shape with an entire edge. After 10 days on WL medium some colonies demonstrate papillae at the edge of the colony. Color sectoring is occasionally seen. On less crowded plates (less than 15 colonies/plate) colony shape is flatter and almost umbonate in configuration.

On glycerol medium (uncrowded plates) morphology after 5 days is smooth, convex, with entire edges. After 10 days many colonies show papillae at the edges. On crowded plates (50 per plate) after 5 days colonies are flatter and concentrically rugose leaving the colony center smooth.

A second strain of bakers yeast NRRL Y-15339 was prepared by the procedure described above, but using the β-glucuronidase cell wall digestion protocol. This yeast had the same balanced baking characteristics as NRRL Y-15338.

This strain differs in having a 64.2±16.0 percent asci and 5.95±1.91 percent four spored asci. After 48 hours on 10° Brix malt extract the cells are ovoid to ellipsoidal in shape. Large cells 7.2×10.4 microns are seen but most of the population is in the 5.7×8.3 micron range. Unmatured, but separated from the mother cell, daughters average 4.0×5.5 microns.

On uncrowded WL medium after 6 days colonies are raised pulvinate to papillate, concentrically colored dark green and light green. The colony edge is entire and dark green, the colony center is dark green with the raised tip lighter in color. On crowded plates the concentric coloring is less pronounced. After 10 days on WL color sectoring and peripheral light papillae are seen.

On uncrowded glycerol medium after 6 days, colonies are white, slightly pulvinate with a flattened rugose or wrinkled edge. This becomes more apparent at 14 days, with some papillae seen at the colony edges. On crowded plates colonies appear the same but the peripheral wrinkling is more pronounced.

The strain ferments melezitose and α-methyl glucoside slowly. With α-methylglucoside gas first appears in the durham tube in 3 days; with melezitose, first gas also accumulates after 3 days. Trehalose is not fermented in 21 days observation.

The following examples illustrate the preparation of the novel yeasts of the present invention.

EXAMPLE

Two separate strains of so-called quick acting sweet dough yeasts are selected. These strains are characterized by ability to grow on glycerol and by being unable to mate in nature.

The two strains of the yeast *Saccharomyces cerevisiae* were cultivated on a culture media containing 0.3% glucose, 1% potassium acetate, 1% yeast extract, 2% peptone, and 1.5% agar for a period of 4 to 5 days. This plate was overlaid with agar containing 0.067 molar concentration of phosphate buffer, pH 7.0, containing 0.1% of TTC and 1.5% agar. After an incubation of 4 to 5 hours as indicated above, two types of colonies were produced, namely grande colonies of pink to red coloration and petite colonies of a white color. The petite colonies are considerably smaller than the grande colonies. This follows the protocol as outlined in Science 125, 198 (1957). The petite colonies were removed and streaked for isolation on yeast extract, peptone and dextrose (YPD), a non-selective media, from this, a master plate was formed which was replicated on a YPGLY plate. The pure sub-clone isolates of the original petite cultures which did not proliferate on the glycerol substrate were cultivated in a flask using a YPD broth media for 48 hours and harvested by centrifugation. The yeast cells were washed free of media with water and recovered.

PROTOPLAST FORMATION

Zymolyase Protocol

The two separate yeast cell cultures from the above procedures were suspended in a zymolyase enzyme cell wall digestion media to form the protoplasts. The protocol involved the inoculation of approximately $5 \times 10^8$ cells into the following medium:

5.0 μL -mercapto-ethanol
100 μg zymolyase
Total volume 2.0 mL buffered 1M sorbitol The cell concentrations in the suspension were about $5 \times 10^8$ cells in 2 mL of total volume of solution. The digestion of the yeast cell walls was microscopically followed and when concluded (about 45 minutes), the protoplasts were washed 5 times with spheroplasting buffer until free of enzymes. The procedure generally follows that of J. Bacteriol. 130, 946-948 (1977). The yeast arising from this protoplast formation protocol following the procedure set out below, was later given the accession number NRRL Y-15338.

β-Glucuronidase Protocol

Another procedure for protoplast formation involves the use of β-glucuronidase enzyme in place of zymolyse in protoplast formation. This β-glucuronidase protocol is as follows:

$5 \times 10^8$ yeast cells were incubated 30 minutes in 0.5M sodium thioglycollate in a 0.1M TRIS pH 8.8 buffer. The yeast cells were harvested by centrifugation, washed once, resuspended in 2 mL buffered 1M sorbitol and 0.1 mL of a 1:10 dilution of β-glucuronidase (Sigma Chemical Co.) was added.

Digestion was followed microscopically. After completion (i.e., about 4 hours), the cells were washed 5 times with spheroplasting buffer. The procedure generally follows J. Molec. Biol. 52, 323-335 (1970).

The yeast which was ultimately obtained following the balance of this procedure set out below, but using the β-glucuronidase protocol, was also deposited at the Northern Regional Research Laboratory and given the accession number NRRL Y-15339.

PROTOPLAST FUSION

The protoplasts to be fused were recovered from the cell wall digestion procedures set out above. These protoplasts were mixed in a fusion buffer containing sorbitol (1M), calcium chloride (0.01M), and 40% polyethylene glycol having a molecular weight range of 4000 to 6000. The mixture of protoplasts was incubated for 30 minutes, centrifuged and the fusion buffer poured off. The procedure used generally follows J. Bacteriol. ibid. Recovery broth was added to the recovered fused yeast protoplasts comprising a 1% yeast extract, 0.2% glucose and 0.8M sorbital which mixture was incubated overnight (12-18 hours) at a temperature of 30° C.

RECOVERY OF HYBRIDS

Reconstituted fused protoplast yeast cells were plated by pour plate techniques using hypertonic glycerol plating media. Cells were incorporated into a molten agar mixture. The hypertonic glycerol plating media contained 1% yeast extract, 2% peptone, 3% glycerol, 0.8M sorbitol and 3% agar. The colonies showing growth on the recovery plate represented only the successful fusion products. These were streaked on YPD plates and selected clones replicated to yeast extract, peptone, sucrose media (YPSUC); a sporulation media containing acetate as the carbon source and a YPGLY media. Selected fused protoplast yeast hybrids were inoculated into YPD broth medium and incubated for 48 hours to determine yield. Those yeasts were selected which had a yield of at least 0.3 g (dry weight) of yeast per 100 mL of broth.

RISE TIME SCREENING

After the first screening for yield described above, the yeast hybrid was harvested and subjected to various further gas output measurement screening tests. These tests involved the addition of 50 mg of yeast solids in 15 mL $H_2O$ to various model dough systems. These systems were (A) 20 g of Pillsbury (4X) flour, 15 mL of water with yeast.
(B) 20 g of Pillsbury (4X) flour, 15 mL of water with yeast, 0.4 g of NaCl had been added.
(C) 20 g of Pillsbury (4X) flour, 15 mL of water with yeast, 4 g of sucrose, 0.4 g of NaCl. In all cases the yeast flour and other ingredients were mixed for 45-60 seconds in each test batch.

Gas evolution was measured ½ hour for a 4 hour period. Only those strains were selected which produced greater than 300 mL of carbon dioxide per 100 mg of yeast solids in rise time test A and 200 mL in rise time tests B and C over the 4 hour test period. The procedure and model dough systems are after Harrison and Burrows, J. Inst. Brew. 65, 35-45 (1959).

Novel strains of bakers yeast prepared according to the procedures described above, which passed the gas tests in the model baking dough systems A, B, and C above, and which yielded 0.3 g yeast/100 mL of broth in growth tests, were propagated in a series of fermenters with a 14 liter last stage fermenter. Molasses yields were 80-85% and considered acceptable. That propagation procedure is set forth in the following example.

MANUFACTURE OF PRESS CAKE YEAST AND ACTIVE DRY YEAST EXAMPLE

The pure culture of the yeast strain *Saccharomyces cerevisiae* NRRL Y-15339 was propagated in a series of laboratory fermenters, the yeast recovered, and reduced in moisture to the cream stage (18-21% solids). Emulsifier (sorbitan monostearate, 1% on yeast solids) or sodium chloride (1-1.5% on yeast solids) was added to the yeast cream which was then reduced to a moisture content of as much as 30 to 90 percent moisture and preferably a moisture content of from about 60% to 70%, particularly 66%, (to form a fresh bakers yeast in a cream, compressed or press cake form) following generally the procedures set forth in Reed and Peppler, *Yeast Technology,* AVI Pub.Co., Westport, Conn. (1973) pp. 83–88.

An active dry yeast is prepared following the procedure generally set forth in Reed and Peppler, ibid. pp. 90–97.

The fresh bakers yeast press cake (66% moisture) containing surface active agent is extruded as a noodle through a perforated plate (0.02-inch orifices) and dried in a commercially available drier, such as a fluidized bed drier made by Aeromatic Co., Mutenz, Switzerland, under controlled humidity conditions (25 to 60 minutes; 220° F. to 100° F.) to a moisture content of about 4.0 to about 6.5% to produce a high activity active dry yeast (HADY). Usually the yeast used to form the noodle has a moisture content of preferably between about 60–70% or 65 to 70% moisture.

This type of yeast, HADY, can be directly added to the dough without reconstitution in water.

An active dry yeast (ADY) is also prepared by a similar procedure using orifice sizes of about 0.065 inch dried to a moisture content of about 7.4–8.2% based on dry yeast solids. This type of yeast (ADY) should be reconstituted in water before mixing with the dough. The results of the fermentation and drying sequence are set forth in the table below for the two strains of bakers yeast NRRL Y-15,338 and NRRL Y-15,339, run by the same procedure as set out below.

TABLE I

| Strain | Molasses Yields | DRY YEAST DATA | | |
|---|---|---|---|---|
| | | % $H_2O$ | % N | % $P_2O_5$ |
| NRRL Y-15338 | 89.0 | 5.34 | 7.12 | 1.99 |
| | 93.1 | 6.14 | 6.48 | 1.87 |
| NRRL Y-15339 | 84.8 | 5.12 | 6.58 | 2.03 |
| | 91.5 | 5.85 | 6.63 | 1.85 |

Bake tests showed the following results.

BAKE TESTS

Bake tests were run on the different yeasts in three different dough systems (i.e., sweet, lean, and regular) using S.J.A. gas measuring equipment. The formulations are as follows:

| REGULAR DOUGH | |
|---|---|
| Premix | |
| 500 g | flour |
| 20 g | sugar |
| 20 g | non-fat dry milk |
| 10 g | salt |
| 15 g | shortening |
| Regular Dough Test | |
| 500 g | of premix (above) |
| 5.5 g | of dry yeast |
| 290 mL | of 50° F. water |

The test ingredients are mixed in a Hobart Model A-120 mixer for 6 minutes. A 250 g aliquot of dough is placed in the S.J.A. gas measuring equipment maintained at 100.4° F. and the gas evolved is measured at 60 and 90 minute intervals. First rise is considered gas production at 60 minutes. The gas production in the period from 60 to 90 minutes (by difference) is considered proof time for purposes of this test, correlatable with commercial operations. The gas volume units are translated into minutes for first rise and proof time using standard curves derived from actual baking trials.

The same procedure is followed in sweet and lean dough systems. The dough formulations and procedure are:

| Sweet Dough | |
|---|---|
| 500 g | of premix (above) |
| 72.0 g | sugar |
| 11 g | dry yeast |
| 250 mL | water at 70° F. |

Procedure: Mix for 8 minutes (Hobart), 155 g of dough placed in a S.J.A. apparatus. Measure gas produced at 60 and 120 minute intervals as exemplary of first rise and proof time as described above.

| Lean Dough | |
|---|---|
| 442 g | Pillsbury 4 × flour |
| 13 g | shortening |
| 8.0 g | salt |
| 5.5 g | dry yeast |
| 300 mL | water, 70° F. |

Procedure: Mix in Hobart 6 minutes. Place a 200 g aliquot of dough in S.J.A. apparatus. Readings of gas evolved are taken at 60 and 90 minute intervals as above and converted to minutes for first rise and proof times.

The yeast strains produced in table I were used in bake tests for regular, sweet, and lean dough systems. The results are shown in table II below.

TABLE II

| | Rise Times (Min.) | | |
|---|---|---|---|
| YEAST STRAIN | Reg. | Lean | Sweet |
| NRRL Y-15338 | 122 | 117 | 124 |
| | 121 | 116 | 124 |
| NRRL Y-15339 | 124 | 112 | 121 |
| | 116 | 115 | 101 |

Minimum standards for performance based on commercial averages are lean dough-122 min; regular-140 min; and sweet-155 min.

A similar yeast propagation fermentation procedure was run in a 200 liter fermentor (Fermatron, New Brunswick Scientific Co.). The results obtained, including the bake tests, are shown in Table III:

TABLE III

| Strain | Molasses | Dry Yeast Data | | Rise Times (min.) | | |
|---|---|---|---|---|---|---|
| | | % N | % $P_2O_5$ | Reg. | Lean | Sweet |
| NRRL Y-15338 | 87.9 | 6.62 | 1.91 | 119 | 116 | 114 |
| NRRL Y-15339 | 91.6 | 6.74 | 2.01 | 123 | 104 | 129 |

The foregoing procedures provide methods for producing novel man made yeast hybrids which are useful in providing to the baking industry an improved baking procedure, especically when the yeast is marketed in the active dry yeast form. They provide an instant active dry yeast of good activity over the entire dough spectrum, but show especially good and superior results in both sweet and lean dough systems. Insofar as it is known, there are no instant active dry yeast on the commercial market which show superior performance in both sweet and lean dough systems. Commercial yeasts are usually selective only for a particular dough system and are so identified by the manufacturer. This versatility permits the commercial baker greater flexibility in his work allowing him to use a single yeast for both these sugar containing systems. This not only minimizes work effort, but also minimizes possible error by the production personnel which could occur by inadvertently using the wrong yeast.

What is claimed is:

1. The biologically pure man made bakers yeast *Saccharomyces cerevisiae* strain NRRL Y-15338.

2. The biologically pure man made bakers yeast *Saccharomyces cerevisiae* strain NRRL Y-15339.

3. A fresh bakers yeast composition obtained from the bakers yeast *Saccharomyces cerevisiae* strain NRRL Y-15338 containing about 30 to 90% moisture.

4. A fresh bakers yeast composition obtained from the yeast *Saccharomyces cerevisiae* strain NRRL Y-15339 containing about 30 to 90% moisture.

5. A bakers yeast composition obtained from bakers yeast *Saccharomyces cerevisiae* strain NRRL Y-15338.

6. A bakers yeast composition obtained from bakers yeast *Saccharomyces cerevisiae* strain NRRL Y-15339 in active dry form.

7. An improved baking process which comprises admixing an instant high activity active dry yeast of the strain *Saccharomyces cerevisiae*, NRRL Y-15338 with a flour to form a dough, permitting the dough mixture to rise, and baking the dough to form a bread or dough product.

8. An improved baking process which comprises admixing an instant high activity active dry yeast of the strain *Saccharomyces cerevisiae*, NRRL Y-15339 with a flour to form a dough, permitting the dough mixture to rise, and baking the dough to form a bread or dough product.

9. The man made yeast strain *Saccharomyces cerevisiae* NRRL Y-15338 made by the protoplast fusion of petite mutant yeast colonies from dissimilar baker's yeast strains of *Saccharomyces cerevisiae* which comprises:
(a) growing yeast strains on a fermentable sugar containing culture medium, the said yeast strains being characterized by a relatively high tolerance to sugar and a capacity for proliferative growth on nutrient substrates in which glycerol is the sole carbon source nutrient,
(b) isolating spontaneous petite mutant yeast colonies which are characterized by their inability to metabolize glycerol,
(c) enzymatically removing the cell wall material to produce yeast protoplasts,
(d) hybridizing the yeast by fusing the yeast protoplasts then in the presence of polyethylene glycol,
(e) recovering the fused hybridized yeast cells from the fusion step,
(f) growing the protoplast fusion yeast cells on a nutrient substrate with glycerol as the sole carbon nutrient source, and
(g) recovering the yeast cells produced by said procedure.

10. The man made yeast strain *Saccharomyces cerevisiae* NRRL Y-15339 made by the protoplast fusion of petite mutant yeast colonies from dissimilar baker's yeast strains of *Saccharomyces cerevisiae* which comprises:
(a) growing yeast trains on a fermentable sugar containing culture medium, the said yeast strains being characterized by a relatively high tolerance to sugar and a capacity for proliferative growth on nutrient substrates in which glycerol is the sole carbon source nutrient,
(b) isolating spontaneous petite mutant yeast colonies which are characterized by their inability to metabolize glycerol,
(c) enzymatically removing the cell wall material to produce yeast protoplasts,
(d) hybridizing the yeast by fusing the yeast protoplasts then in the presence of polyethylene glycol,
(e) recovering the fused hybridized yeast cells from the fusion step,
(f) growing the protoplast fusion yeast cells on a nutrient substrate with glycerol as the sole carbon nutrient source, and
(g) recovering the yeast cells produced by said procedure.

* * * * *